United States Patent [19]

Marquis

[11] 4,071,540
[45] Jan. 31, 1978

[54] ANHYDRIDE SEPARATION PROCESS

[75] Inventor: David M. Marquis, Lafayette, Calif.

[73] Assignee: Chevron Research Company, San Francisco, Calif.

[21] Appl. No.: 712,413

[22] Filed: Aug. 6, 1976

Related U.S. Application Data

[63] Continuation-in-part of Ser. No. 703,478, July 8, 1976, abandoned, which is a continuation of Ser. No. 550,070, Feb. 14, 1975, abandoned, which is a continuation-in-part of Ser. No. 452,488, March 18, 1976, abandoned.

[51] Int. Cl.$^2$ .................. C07D 307/60; C07D 307/89
[52] U.S. Cl. .......................... 260/346.76; 260/346.75; 260/346.7
[58] Field of Search ...................... 260/346.8 M, 346.7

[56] References Cited

U.S. PATENT DOCUMENTS 3,850,758 11/1974 Smith et al. ...................... 260/346.8
3,891,680 6/1975 Katsumoto et al. .............. 260/346.8

Primary Examiner—Henry R. Jiles
Assistant Examiner—Bernard Dentz
Attorney, Agent, or Firm—D. A. Newell; John Stoner, Jr.; W. Keith Turner

[57] ABSTRACT

An absorption process for separating a maleic or phthalic anhydride from a gaseous mixture containing the anhydride which comprises contacting the gaseous mixture with a liquid absorbent comprising polymethylbenzophenones, at least a portion of which benzophenones contain at least 3 methyl groups, at a temperature for the absorbent between about 20° and 235° C and at a pressure sufficient to effect absorption of the anhydride into the absorbent. Preferably the absorption process is used to remove maleic anhydride from a gas stream, preferably the absorbent includes dixylylketone, and preferably the absorption is carried out by countercurrent contacting in an absorber column.

13 Claims, 1 Drawing Figure

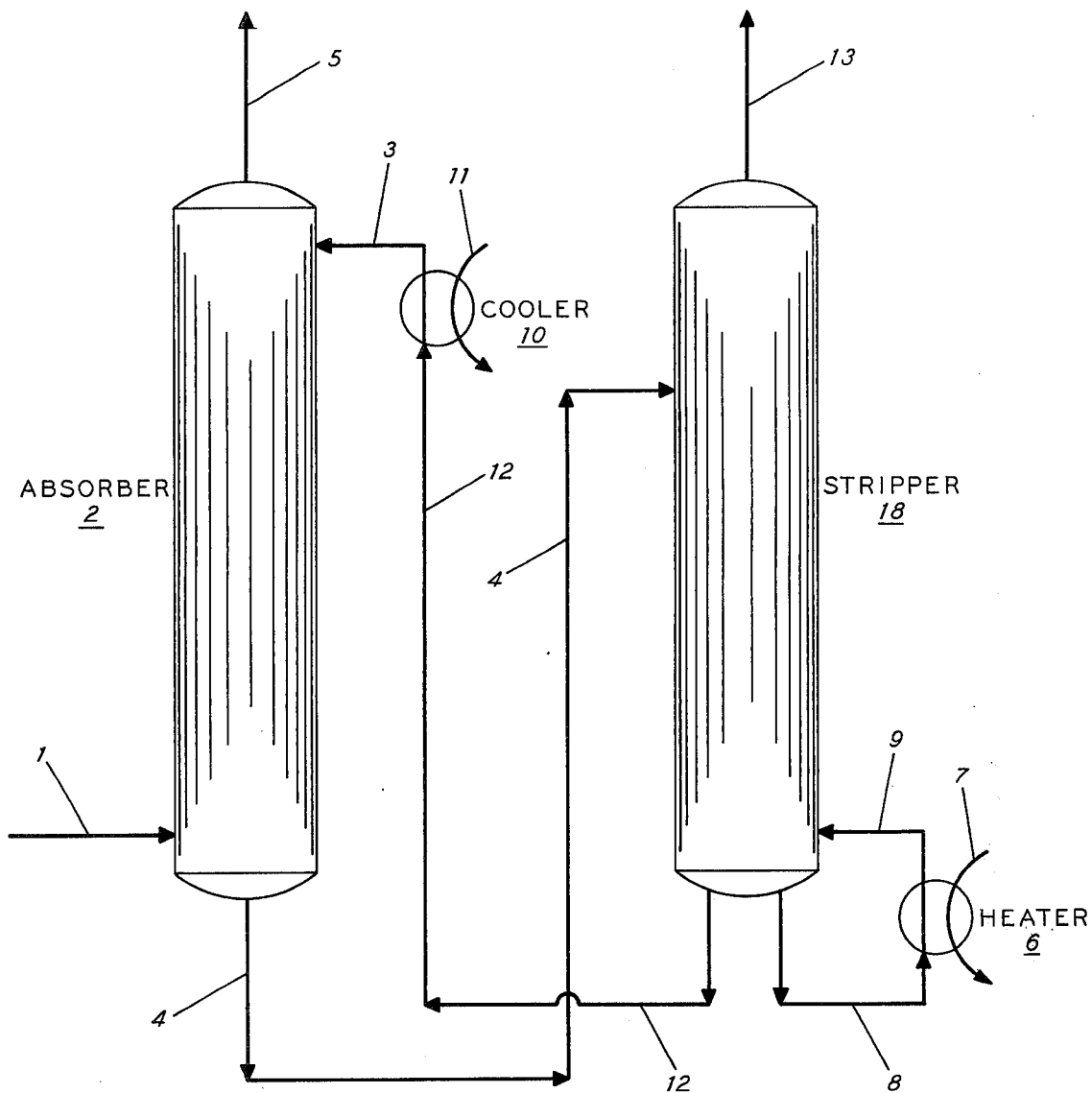

ANHYDRIDE SEPARATION PROCESS

CROSS-REFERENCE TO RELATED APPLICATION

This application is a continuation-in-part of U.S. application Ser. No. 703,478 filed July 8, 1976 now abandoned, which in turn is a continuation of U.S. Pat. Ser. No. 550,070 filed Feb. 14, 1975 now abandoned, which in turn is a continuation-in-part of U.S. application Ser. No. 452,488, filed Mar. 18, 1974 now abandoned.

BACKGROUND OF THE INVENTION

The present invention relates to separation of maleic anhydride or phthalic anhydride from a gaseous mixture containing the anhydride, particularly by the use of an organic absorbent.

Phthalic anhydride and maleic anhydride are both important industrial chemicals which are produced by vaporphase oxidation of a hydrocarbon feedstock in an oxidation reactor, followed by recovery and then purification of the anhydride. The most common feedstocks for phthalic anhydride plants are naphthalene and orthoxylene; for maleic anhydride plants, the most common feedstock is benzene, although other hydrocarbon feeds have been disclosed, including butene and butane.

Recovery of the anhydride from the gaseous effluent stream from the oxidation reactor can be done by scrubbing the effluent with water, which results in conversion of the anhydride to an acid. The acid then needs to be dehydrated to produce the anhydride product.

In the case of phthalic anhydride (b.p. = 285° C), condensation of the anhydride present in the reactor gaseous effluent can be done to separate the phthalic anhydride. Frequently maleic anhydride (b.p. = 202° C) is recovered by the condensation of a part of the maleic anhydride and maleic acid in the gaseous effluent, the remainder being recovered by scrubbing with water, resulting in an aqueous maleic acid solution. Then both the partial condensate and the aqueous acid solution must be dehydrated to obtain product maleic anhydride.

Recovery of maleic anhydride or phthalic anhydride from the oxidation reactor effluent using an organic absorbent as opposed to an aqueous absorbent has also been disclosed. For example, U.S. Pat. No. 2,574,644 discloses the use of dibutylphthalate for the recovery of maleic anhydride or phthalic anhydride from an oxidation reactor effluent stream. According to the process disclosed in U.S. Pat. No. 2,574,644, the oxidation reactor effluent is cooled to first condense a portion of the anhydride vapor. The remaining gaseous stream is contacted with the dibutylphthalate absorbent to remove the remaining uncondensed anhydride by absorption into the absorbent. The resulting rich absorbent is stripped to obtain a product anhydride stream.

British Pat. No. 727,828 discloses the use of dibutylphthalate for simultaneous absorption of both maleic anhydride and phthalic anhydride at absorbent temperatures above 40° C.

U.S. Pat. No. 3,040,059 discloses the use of molten wax as an absorbent for removing maleic anhydride or phthalic anhydride from an oxidation reactor effluent stream.

U.S. Pat. No. 2,893,924 discloses the use of diphenylpentachloride absorbent as well as tricresyl phosphate as an absorbent for removing maleic anhydride or phthalic anhydride by absorption.

Japanese Pat. No. 35-7460 discloses the use of dibutylmaleate as an organic absorbent for removing maleic anhydride from gas streams, and Japanese Pat. No. 32-8048 discloses the use of dimethylterephthalate for removing maleic anhydride from gas streams containing maleic anhydride.

U.S. Pat. No. 3,891,680 discloses the use of certain dialkylphthalates as absorbents for removal of maleic anhydride from gas streams containing maleic anhydride.

Also, U.S. Pat. No. 3,818,680 discloses alkyl or alkenyl succinic anhydrides, in general intramolecular carboxylic acid anhydrides, as absorbents for the removal of maleic anhydride from gas streams. The disclosures of U.S. Pat. Nos. 3,891,680 and 3,818,680, especially in that they relate to the use of organic absorbents for maleic anhydride removal, are incorporated herein by reference.

These prior art absorbents have drawbacks which have prevented their acceptance and use in commercial applications. The ester-type absorbents — dialkylphthalates, maleates, etc. — can undergo some transesterification with maleic anhydride and also can decompose to give some anhydride and alcohol; all of these by-products contaminate the maleic anhydride product. The polychlorinated biphenyls are hazardous to the environment and are essentially forbidden by law. Molten wax has limited solubility for maleic anhydride. As a consequence, commercial maleic anhydride plants use water recovery or a system or switch condensers, and no organic-media recovery units are presently in operation.

Typical prior art absorption schemes involve the use of what is frequently called a "figure-8 loop". The figure 8 is formed by the absorbent entering the top of the absorber, flowing downwardly therein, and then being transferred as rich absorbent to the absorber stripper, flowing downwardly in the stripper and then being transferred as lean absorbent to the upper part of the absorber to complete the figure-8 loop. In the absorber, the absorbent absorbs the solute and in the stripper the solute is distilled out of the absorbent. Distillation is typically accomplished by generating upflow vapors through heat input to the lower part of the stripper.

For example, the above-mentioned U.S. Pat. No. 2,574,644 shows an anhydride absorption scheme wherein basically a figure-8 loop is used.

A common problem in separation of a constituent from a gas mixture by countercurrent absorption in an absorber column is loss of absorbent out of the top of the column with the lean or scrubbed gas stream flowing out the top of the column. The loss is caused by the entrainment and vaporization of absorbent into the upwardly flowing lean gas stream. Entrainment can be reduced by using a deentrainment device such as a demister pad and by reducing gas flow rates through the column. Vapor losses of absorbent can be reduced by using a lower temperature, using a higher pressure, and use of less volatile solvents, if such solvents are available.

U.S. Pat. No. 3,850,758 shows the purification of crude maleic anhydride using dimethylbenzophenone by heating the maleic anhydride in the dimethylbenzophenone at a temperature above 230° C and at total reflux for at least 15 minutes, and then recovering maleic anhydride by distillation. The U.S. Pat. No. 3,850,758 also mentions the use of dimethylbenzophenone as a recovery solvent for maleic anhydride produced by gas phase oxidation of organic compounds and employing the same dimethylbenzophenone in the purification process.

SUMMARY OF THE INVENTION

According to the present invention, an absorption process is provided for separating a maleic or phthalic anhydride from a gaseous mixture containing the anhydride which process comprises contacting the gaseous mixture with a liquid absorbent comprising polymethylbenzophenones, at least a portion of which benzophenones contain at least 3 methyl groups, at a temperature for the absorbent between about 20° and 235° C and at a pressure sufficient to effect absorption of the anhydride into the absorbent.

For the purposes of this invention, polymethylbenzophenones are benzophenones having a total of from 2 to 5 methyl groups, with at least 1 methyl group in each aromatic ring. Polymethylbenzophenones include, among others, toluylxylylketones, dixylylketones, xylyltrimethylphenylketones, etc. Polymethylbenzophenones have the following structure:

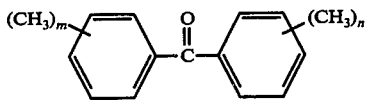

wherein m and n have the value of 1, 2, 3 or 4 and the sum of m plus n is 2, 3, 4 or 5. Preferably tetramethylbenzophenones; most preferably dixylylketones, comprise at least 20% of the absorbent composition, e.g., 20 weight percent to 100 weight percent of the absorbent.

Dixylylketones are tetramethyldiphenylketones, also called tetramethylbenzophenones, having 2 methyl groups in each aryl ring, as shown in the following chemical formula:

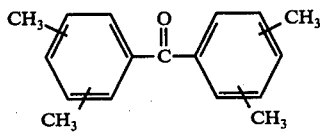

wherein the methyl groups occupy two of the five free ring positions in each ring.

Among other factors, the present invention is based on the finding that polymethylbenzophenones, and especially dixylylketones or mixtures containing dixylylketones, are highly effective as maleic anhydride absorbents; they are good solvents for maleic anhydride, they are stable to hot, oxidizing gases, and have a low vapor pressure.

Preferably the absorption process of the present invention is carried out at a temperature between 65° and 125° C, more preferably between about 65° C and 95° C. The maleic anhydride-rich gas stream may enter the absorption process or absorber column at a temperature above the preferred range, and the liquid absorbent may enter at a temperature below the preferred range, but in the main it is preferred that the absorption be carried out within the aforesaid ranges.

In accordance with a preferred embodiment of the present invention, an absorption process for separating maleic anhydride from a gaseous mixture containing maleic anhydride is provided, which process comprises:

a. feeding a stream of liquid absorbent comprising polymethylbenzophenones, at least a portion of which benzophenones contain at least 3 methyl groups, to an absorber column;

b. feeding a stream of the gaseous mixture to the absorber column;

c. countercurrently contacting the liquid absorbent and the gaseous mixture in the absorber column at a temperature for the absorbent between about 20–235° C to obtain maleic anhydride-rich absorbent and a gas stream lean in maleic anhydride; and d. recovering the absorbent rich in maleic anhydride and exhausting the gas stream lean in maleic anhydride.

Preferably the liquid absorbent is fed in accordance with step (a) above to the upper part of the absorber and the gas stream is fed in accordance with step (b) above to the lower part of the absorber. The term "upper part" is used to mean about the uppermost one-quarter of the column. As illustrated in the drawing, more preferably the absorbent is fed to approximately the top of the absorber column. The term "lower part" is used to mean about the lowermost one-quarter of the column. As illustrated in the drawing, more preferably the maleic anhydride-rich gas stream is fed to approximately the bottom of the absorber.

The absorbent used in the process of the present invention must contain polymethylbenzophenones, at least a portion of which benzophenones contain at least 3 methyl groups. The absorbent can contain other constituents, particularly other polyalkyl-substituted benzophenones having a boiling point in the range of 315–360° C, preferably 315–350° C. For example, the following substances may be used in the process of the present invention:

dimethylbenzophenones such as
    2,2'-dimethyldiphenylketone,
    2,3'-dimethyldiphenylketone,
    3,4'-dimethyldiphenylketone,
    4,4'-dimethyldiphenylketone,
    3,3'-dimethyldiphenylketone,
    2,4'-dimethyldiphenylketone;
trimethylbenzophenones such as
    2,3,2'-trimethyldiphenylketone,
    2,4,4'-trimethyldiphenylketone,
    3,5,3'-trimethyldiphenylketone,
    2,5,4'-trimethyldiphenylketone,
    2,6,2'-trimethyldiphenylketone,
    3,4,3'-trimethyldiphenylketone,
    3,5,3'-trimethyldiphenylketone;
tetramethylbenzophenones such as
    2,3,2',3'-tetramethyldiphenylketone,
    2,3,3',4'-tetramethyldiphenylketone,
    2,3,2',4'-tetramethyldiphenylketone,
    2,3,2',5'-tetramethyldiphenylketone,
    2,4,2',4'-tetramethyldiphenylketone,
    2,4,2',5'-tetramethyldiphenylketone,
    2,4,2',6'-tetramethyldiphenylketone,
    2,5,2',5'-tetramethyldiphenylketone,
    2,5,2',6'-tetramethyldiphenylketone,
    2,6,2',6'-tetramethyldiphenylketone;
pentamethyldiphenylketones such as
    2,3,4,2',3'-pentamethyldiphenylketone,
    2,4,6,3',5'-pentamethyldiphenylketone,
    2,3,5,2',6'-pentamethyldiphenylketone,
    2,4,5,2',5'-pentamethyldiphenylketone,
    2,3,6,3',4'-pentamethyldiphenylketone,
ethylxylylketones such as
    2,3-dimethyl-4'-ethyldiphenylketone, 2,4-dimethyl-2'-ethyldiphenylketone,
2,5-dimethyl-3'-ethyldiphenylketone;
diethyldiphenylketones such as
2,4'-diethyldiphenylketone, and
3,3'-diethyldiphenylketone.

Preferably the ethyl-substituted diarylketones are minimized.

Preferably the amount of tetramethylbenzophenone in the liquid absorbent is at least about 20 weight percent, more preferably at least about 30 weight percent. A particularly preferred liquid absorbent is one consisting essentially of a dixylylketone or isomers of dixylylketone. Another particularly preferred absorbent is one consisting essentially of about equal parts of ditolylketone, dixylylketone and tolylxylylketone, more preferably one part ditolylketone, one part dixylylketone and two parts by weight tolylxylylketone.

The absorption process of the present invention can be applied to the removal of phthalic anhydride as well as maleic anhydride from gaseous mixtures. However, the absorption process is especially advantageously applied to the removal of maleic anhydride from gaseous mixtures.

Preferably the gaseous mixture fed to the absorption process of the present invention is the gaseous effluent from an oxidation reactor of either a phthalic anhydride plant or a maleic anhydride plant, which contains nitrogen, oxygen, water and carbon dioxide, as well as the product phthalic or maleic anhydride vapors. maleic anhydride vapors condensed in the presence of water react to form maleic acid, which can then partially isomerize to fumaric acid. It has been found that the process of the present invention is especially advantageous in that it can be applied to the separation of maleic anhydride from the gaseous effluent of a maleic anhydride plant hydrocarbon oxidation reactor at sufficiently high temperatures to substantially avoid the concurrent formation of maleic and fumaric acids. These temperatures usually are in the range of 120° to 175° for the gaseous feed to the absorber in the case of maleic anhydride production.

The high temperature absorption has been found to be successfully carried out without appreciable degradation of the polymethylbenzophenone absorbent, particularly including the dixylylketone absorbent, even though the gases from which the maleic anhydride is absorbed are hot and contain oxygen. Typical composition of the feed to the absorber in the case of maleic anhydride production is by volume 5–20% oxygen, 0.2–5% n-butane, (or other hydrocarbon) 1–4% carbon dioxide, 1.5–6% carbon monoxide, 0.3 to 2% maleic anhydride, water vapor 2–10%, and the balance nitrogen.

The process of the present invention is particularly advantageously applied to maleic anyhydride separation from the effluent from a 4-carbon hydrocarbon (e.g., butane, n-butenes or butadiene) oxidation process wherein maleic anhydride is produced using a vanadium oxide-phosphorus oxide catalyst, for example, an n-butane oxidation utilizing those catalysts as disclosed in U.S. Pat. No. 3,864,280.

The terms "gas" or "gaseous" are used herein to include vapors as well as substances which are normally gaseous at room temperature and pressure. Thus, the effluent from an oxidation reactor, even after some cooling, typically will contain some water vapor, and for ease of description such an effluent stream is still called a gaseous mixture.

The temperature of the gaseous feed to the absorption process of the present invention preferably is sufficiently high to maintain all the components of the gas feed in the vapor (gaseous) phase. Thus, in the case of maleic anhydride, the temperature normally should be above 95° C, preferably above 110° C, and usually between about 120° and 175° C. Of course, the exact temperature to maintain vapor phase depends on the pressure as well as the composition of the gas stream fed to the absorption process of the present invention. Preferably the entire product effluent stream from the hydrocarbon oxidation reactor is processed in the absorption step of the present invention.

BRIEF DESCRIPTION OF THE DRAWING

The drawing is a schematic flow diagram illustrating a preferred embodiment of the present invention.

FURTHER DESCRIPTION OF THE DRAWING AND EXAMPLES

Referring to the drawing, a gaseous mixture containing anhydride is fed via line 1 to absorber 2. This gaseous mixture is generally sufficiently hot to be above the condensation point of any component in the mixture; for example, in the case of maleic anhydride produced by air oxidation of a hydrocarbon, the condensation point is generally between about 95° and 120° C, depending on the pressure and the composition of the gas, particularly the water content. The gaseous mixture is typically generated by air oxidation of a hydrocarbon stream to produce an anhydride as described in various prior art references on production of maleic anhydride or phthalic anhydride by oxidation of a hydrocarbon.

The gaseous mixture from the oxidation of the hydrocarbon is usually cooled to a temperature in the range 120° C to 165° C, preferably 130°–140° C, more preferably 135°–140° C, before it is fed to absorber 2. The pressure of the gaseous mixture feed to the absorber is usually between 1 and 50 psig, typically about 3–30 psig.

In absorber 2, the anhydride is scrubbed out of the gas mixture by a liquid absorbent comprising the polymethylbenzophenones. The absorbent is introduced to the absorber via line 3, and flows downwardly in the absorber in countercurrent contact to the upwardly flowing gaseous mixture. By the time the gaseous mixture reaches the top of the absorber, it is substantially free of anhydride. The exiting gaseous mixture can be referred to as a lean gas mixture, as it is, of course, quite lean in maleic anhydride compared to the feed gaseous mixture, which is rich in maleic anhydride. Typical maleic anhydride contents for the feed gas mixture and the exiting lean gas mixture are about 0.3 to 1.2 volume percent for the feed gas mixture and 0.003 to 0.012 volume percent for the exiting gas mixture. The lean gas mixture exits via line 5. The anhydride-rich absorbent leaves the bottom of the absorber via line 4.

In stripper 18, the rich absorbent is stripped of the anhydride solute. The stripped anhydride product leaves the stripper via line 13. The stripping requires a heat input as indicated by heater 6. As indicated in the drawing, heat input is accomplished by a hot fluid flowing through heater 6, as indicated by line 7, countercurrent to absorbent material introduced to the heater via line 8. Hot, partially vaporized absorbent is withdrawn from heater 6 and is introduced to stripper 18 via line 9.

The stripper may be called a distillation column, especially since in anhydride recovery there is typically no injected stripping gas, but rather the stripping is typically effected by the use of a reboiler and distillation column. In any case, it is important that the absorbent be separated from the dissolved anhydride, and this separation operation can be termed either "stripping" or "distillation". The purified absorbent resulting from the stripping can be termed "lean" absorbent. The lean absorbent is withdrawn from the bottom of stripper 18 via line 12.

The lean absorbent can be cooled before being fed to absorber 2. As shown in the drawing, the absorbent is cooled in cooler 10 by heat exchange with countercurrently flowing liquid, as indicated by arrow 11. For further removal of heat from the gas stream in a commercial scale (adiabatic) absorption column, a portion of the absorbent flowing downward can be sent through a cooler and returned to the column. Desirably, the absorbent is taken from the lower part of the column, cooled, and returned at a higher point whose location is determined by standard calculations. In prior art processes, the heat removal from the absorber column is typically accomplished by means such as cooler 10, or perhaps also by introducing a cool reflux stream or its equivalent to the top of the absorber column.

EXAMPLE

The following example further illustrates the method of the invention. The absorption agent was a mixture of isomeric dixylylketones prepared by reaction of phosgene with a mixture of xylene isomers (25% para, 60% meta and 15% ortho), using alumnium chloride catalyst. This solvent, purified by distillation, had a normal boiling range of 334°–347° C. The maleic anhydride-containing gas was the effluent stream from the oxidation of an n-butane/air mixture in a vapor-phase fixed-bed reactor. This stream contained about 0.6 volume percent of maleic anhydride. The contacting of the effluent oxidate gas stream with the dixylylketone was effected in a 2"-ID, 30 sieve-tray column. Separation of maleic anhydride and absorbent was carried out in a 1"-ID, 10-sieve-tray column.

This example was carried out by the process shown in the drawing. The process was carried out until steady-state operation was established. Then measurements were made as to absorption efficiency, maleic anhydride recovery, maleic anhydride quality and solvent loss.

The feed gas, 16.8 normal (measured at 1 atm. and 21° C) cubic feet per hour and containing 1.13 pounds of maleic anhydride per 1000 cubic feet, was passed via line 1 into absorber 2, having a temperature of 76° C. The absorber was maintained at 10 psig pressure. At the same time, 100 g per hour of dixylylketone was charged to the absorber via lines 12 and 3. The off-gases, containing 0.002 pounds of maleic anhydride per 1000 cubic feet, were vented through line 5. The absorbent, now containing 7.5% (weight) maleic anhydride, was removed from the absorber column via line 4 and charged to tray 2 of the distillation column at a rate of 1.16 pounds per hour.

The stripper (distillation) column was maintained at an average pressure of 50 torr. The reboiler temperature was maintained at 246° C, and dixylylketone absorbent containing 0.4% (weight) of maleic anhydride was removed through line 12 and recycled to the absorber column.

Maleic anhydride product was taken overhead through line 13 and removed through line 13. This maleic anhydride product had a freezing point of 52.53° C (theory, 52.8° C), and it was 99.6% pure by gas chromatographic analysis. There was less than 0.1 weight percent of fumaric acid made throughout the run.

The procedure was repeated through 4 recycles. For simplicity, the following table summarizes only the results of the initial and 4th recycle operations.

|  | Initial | 4th Recycle |
|---|---|---|
| Absorber |  |  |
| Pressure, psig | 77 | 76 |
| Weight absorbent fed, g | 10 | 10 |
| Weight % maleic anhydride | 2137 | 1867 |
| in absorbent fed | 0 | 0.38 |
| Absorbent/gas ratio, g/NCF | 6.1 | 6.1 |
| Stripper |  |  |
| Pressure, mm Hg | 50 | 50 |
| Overhead temperature, ° C. | 116 | 116 |
| Reboiler temperature, ° C. | 243 | 246 |

Another polymethylbenzophenone mixture was prepared by the reaction of phosgene with a mixture of aromatic hydrocarbons comprising 50% toluene, 12% paraxylene, 30% metaxylene, and 8% orthoxylene. The product had a boiling point range of 323°–351° C. Calculations based on vapor pressure of this mixture and of maleic anhydride indicate that the recycle absorbent stream in line 12 will have less than 0.4% (weight) of maleic anhydride, all other factors being the same as in the above-described example.

I have found that the use of an absorbent comprising dixylylketone with at least a minor amount of material boiling below dixylylketone is especially advantageous in the process of the present invention for achieving high absorption efficiency and relative ease of regeneration of the absorbent, as for example in a steam-heated absorbent stripper, particularly a steam-heated reboiler of the stripper. Thus, an absorbent comprising tolylxylylketone and one or more dixylylketones, and absorbents comprising ditolylketone and one or more dixylylketones, are especially preferred absorbents.

I claim:

1. An absorption process for separating maleic or phthalic anhydride from a gaseous mixture containing the anhydride which comprises contacting the gaseous mixture with a liquid absorbent comprising polymethylbenzophenones, at least a portion of which benzophenones contain at least 3methyl groups, at a temperature for the liquid absorbent between about 20° and 235° C and at a pressure sufficient to effect absorption of the anhydride into the absorbent.

2. A process in accordance with claim 1 wherein the absorbent comprises at least 20 weight percent dixylylketone or dixylylketones.

3. A process in accordance with claim 2 wherein the anhydride is maleic anhydride.

4. A process in accordance with claim 3 wherein the temperature is between about 65° C and 125° C.

5. A process in accordance with claim 3 wherein the temperature is between about 65° and 95° C.

6. A process in accordance with claim 3 wherein the absorbent consists essentially of a mixture of di-, tri- and tetramethylbenzophenones.

7. A process in accordance with claim 3 wherein the absorbent consists essentially of one or more dixylylketones.

8. An absorption process for separating maleic anhydride from a gaseous mixture containing maleic anhydride which comprises:
   a. feeding a stream of a liquid absorbent comprising a dixylylketone to an absorber column;
   b. feeding a stream of the gas mixture to the absorber column;
   c. countercurrently contacting the liquid absorbent and the gaseous mixture in the absorber column at a temperature between about 20° and 235° to obtain maleic anhydride-rich absorbent and a gas stream lean in maleic anhydride; and
   d. recovering an absorbent rich in maleic anhydride and the gas stream lean in maleic anhydride.

9. A process in accordance with claim 8 wherein the temperature is between about 65° and 125° C.

10. A process in accordance with claim 8 wherein the liquid absorbent is fed in accordance with step (a) to the upper part of the absorber and the gas stream is fed in accordance with step (b) to the lower part of the absorber.

11. A process in accordance with claim 8 wherein the absorbent consists essentially of a mixture of di-, tri- and tetramethylbenzophenones.

12. A process in accordance with claim 8 wherein the absorbent consists essentially of a dixylylketone or dixylylketone isomers.

13. A process in accordance with claim 8 wherein the gas mixture containing maleic anhydride is an effluent stream from an oxidation reactor of a maleic anhydride production plant for the conversion of a hydrocarbon feed to a maleic anhydride product.

* * * * *